United States Patent
Richter et al.

[11] Patent Number: 5,914,383
[45] Date of Patent: Jun. 22, 1999

[54] ISOCYANATE TRIMERS CONTAINING IMINOOXADIAZINE DIONE GROUPS, THEIR PREPARATION AND USE

[75] Inventors: Frank Richter, Leverkusen; Josef Pedain; Harald Mertes, both of Köln; Carl-Gerd Dieris, Dormagen, all of Germany

[73] Assignee: Bayer Aktiengesellschaft, Leverkusen, Germany

[21] Appl. No.: 08/822,072

[22] Filed: Apr. 30, 1997

[30] Foreign Application Priority Data

Mar. 26, 1996 [DE] Germany .............................. 19611849

[51] Int. Cl.$^6$ ........................ C08G 18/12; C07D 229/00; C07D 251/34; C07D 273/04
[52] U.S. Cl. .............................. 528/59; 528/67; 540/200; 540/202; 540/356; 540/364; 544/67; 544/221
[58] Field of Search ........................ 528/59, 67; 540/200, 540/202, 356, 364; 544/67, 221

[56] References Cited

U.S. PATENT DOCUMENTS

| | | | |
|---|---|---|---|
| 4,160,080 | 7/1979 | Köenig et al. | 528/59 |
| 4,801,663 | 1/1989 | Ueyanagi et al. | 525/528 |
| 4,992,548 | 2/1991 | Scholl et al. | 544/193 |
| 5,013,838 | 5/1991 | Scholl | 544/193 |
| 5,298,431 | 3/1994 | Goldstein et al. | 528/491 |

FOREIGN PATENT DOCUMENTS

| | | |
|---|---|---|
| 1335990 | 6/1995 | Canada . |
| 196 03 736 | 8/1997 | Germany . |
| 1153815 | 5/1969 | United Kingdom . |

OTHER PUBLICATIONS

J. Prakt. Chem. 336 (Month unavailable) (1994) 185–200.
Ch. Zwiener, L. Schfmalstieg, M. Sonntag, K. Nachtkamp and J. Pedain, Farbe und Lack Dec. 1991, 1052–1057 and bibliography.
Chem. Ber. (Month unavailable) 1927, 60, 295.
Chem Ber. Mar. 1987, 120, 339.
J. Chem Soc., Sep. 11th, 1945, 864–865.
Holleman–Wiberg, Lehrbuch der Anorganischen Chemie [Inorganic Chemistry Textbook], 91st–100 editions, W. de Gruyter Verlag, Berlin NY, (month unavailable) 1985, p. 408, footnote 50.

*Primary Examiner*—Yogendra N. Gupta
*Attorney, Agent, or Firm*—Joseph C. Gil; Thomas W. Roy

[57] ABSTRACT

The present invention relates to a polyisocyanate mixture containing isocyanate trimers provided that
i) 30 to 100 mole percent of the trimers are iminooxadiazine diones B and

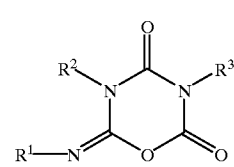

B ii) 0 to 70 mole percent of the trimers are isocyanurates A
iii) less than 10 mole percent of the polyisocyanate mixture is of the uretone imine structural type, and
iv) the ratio of the sum of the mole percents of trimers A and B to the mole percent of uretdiones is greater than 4:1
wherein $R^1$, $R^2$ and $R^3$ are the same or different and represent the groups obtained by removing an isocyanate group from an aliphatic, cycloaliphatic, aromatic and/or araliphatic isocyanate having an NCO content of less than 70% and/or their oligomers.

The present invention also relates to a process for the preparation of these isocyanate trimers, mixtures of these isocyanate trimers with other polyisocyanates and compositions containing these isocyanate trimers, in which the isocyanate groups may optionally be blocked with blocking agents, and compounds containing two or more isocyanate-reactive groups.

6 Claims, No Drawings

ISOCYANATE TRIMERS CONTAINING IMINOOXADIAZINE DIONE GROUPS, THEIR PREPARATION AND USE

BACKGROUND OF THE INVENTION

1. Field of the Invention

The invention relates to isocyanate trimers containing iminooxadiazine dione groups, a process for their preparation and their use for preparing coatings, adhesives and plastics.

2. Description of the Prior Art

It is known to convert isocyanates by trimerization into isocyanurates (1,3,5-substituted hexahydro-s-triazine-2,4,6-triones; no data is given hereinbelow as to the degree of hydrogenation of the heterocycles such as "hexahydro", reference being made in a general manner to species having single bonds in the ring). The 1,3,5-triphenyl derivative, which is obtainable, for example, by trimerizing phenylisocyanate in the presence of potassium acetate, was synthesized for the first time in 1885 (A. W. Hofmann, Chem. Ber. 1885, 18, 765 et seq.). Although other methods are also possible for synthesizing isocyanurates (cf. H. F. Piepenbrink, "Houben/Weyl, Methoden der Organischen Chemie" 4th edition, Vol. VIII, Oxygen Compounds III, G. Thieme Verlag, Stuttgart, 1952, ed. E. Müller, p. 244 et seq.), the simplest way is still to trimerize isocyanates.

In particular isocyanurate polyisocyanates which are accessible as a result of trimerizing commercially available diisocyanates, such as tolylene diisocyanate (TDI), bis(isocyanatophenyl) methane and polyphenylene polymethylene polyisocyanates as prepared by aniline-formaldehyde condensation followed by phosgenation (MDI), hexamethylene diisocyanate (HDI), isophorone diisocyanate (IPDI) and bis(isocyanatocyclohexyl) methane ($H_{12}MDI$), have proven to be qualitatively high-grade raw materials, inter alia, for the preparation of polyurethane plastics materials and polyurethane coatings. Furthermore, trimerization is a conventional cross-linking reaction, in particular in the case of aromatic polyisocyanates, for preparing high molecular weight, optionally foamed, plastics.

These prior art systems exhibit some disadvantages. If, for example, diisocyanates are trimerized in order to prepare isocyanurate polyisocyanates which are viable, in particular in the lacquers and coatings sector, the (melt) viscosity of the resulting polyisocyanates is sometimes extremely high. This is particularly the case when working with high degrees of conversion or high resin yields, which may sometimes result in problems in working or utilizing these products.

On the other hand, however, a high degree of conversion is desirable for a number of reasons. For instance, there are important economic factors to consider because of the time- and energy-consuming separation of the monomer after the trimerization reaction, which is required from an environmental standpoint. Then there is the increase in the NCO functionality (f) of the trimers which is associated with the increasing degree of conversion of starting diisocyanate as a result of the formation of product constituents containing more than just one isocyanurate ring. This again is highly desirable because products having a high cross-link density and also high physical and chemical stability are obtained in this way. For the sake of simplicity these species will be characterized hereinbelow by the number of diisocyanate molecules, n, which are incorporated (n=3,5,7, . . . ). If n=3, f=3, when n=5, f=4, etc. However, as n increases so does the (melt) viscosity of the polyisocyanate trimers.

Consequently, in order to prepare low viscosity trimers either the reaction must be terminated at a very low conversion, in order to obtain as high a proportion as possible of "n=3" trimer in the mixture, or the "n=3" species is separated subsequently out of oligomer mixtures, optionally also only in enriched form (cf. DE-A 3,810,908; WO-A 93/07 183). Neither one of the two methods is advantageous in economic terms. Low conversion rates result in heavy losses in resin yield, which as previously indicated means a high economic cost, and regardless of the type of separation, the process necessarily results in a by-product of higher viscosity fractions in addition to increased process costs. Furthermore, it can be difficult when carrying out industrial trimerization to obtain reproducible uniform products if further reaction has to be interrupted even after a very short time (homogenization problems, incomplete side reactions and secondary reactions between co-catalysts which are frequently co-used, etc.).

A number of substances and processes have therefore been proposed to reduce the viscosity of lacquer polyisocyanates. One involves the use of reactive thinners, i.e., substances which exhibit a low intrinsic viscosity, normally below 300 mPa•s at 23° C., and have groups which are capable of reacting with reaction partners of the polyisocyanates, for example, polyhydroxyl compounds. Polyisocyanates based on aliphatic diisocyanates (especially HDI) and containing uretdione groups ("dimers") and/or allophanate structure have been used for this purpose. (H. J. Laas et al., J. Prakt. Chem. 1994, 336. 196–198).

It is generally immaterial in terms of the final viscosity of the polyisocyanate mixture whether the mixture was produced by the simultaneous formation of the high viscosity isocyanurates and low viscosity allophanates or whether separately produced products are mixed subsequently.

Both uretdione group-containing and also allophanate polyisocyanates (provided that the allophanates have been obtained from diisocyanates and monoalcohols) are primarily difunctional. Allophanates based on higher functional alcohols exhibit no viscosity advantages over biuret polyisocyanates or isocyanurate polyisocyanates (DE-A 2,729, 990). Regardless of which type of low viscosity reactive diluent is used, the functionality of the polyisocyanate mixture is lowered. To significantly lower the viscosity in HDI polyisocyanates, such high concentrations of difunctional reactive thinners are necessary that the functionality of the resulting mixture is already markedly below 3 (DE-A 19,603,736).

A further factor is that the uretdione four-membered ring is thermally unstable and dissociation into the starting diisocyanates takes place at elevated temperature. In the case of prior art low viscosity uretdione reactive thinners, which are obtained, for example, in accordance with DE-A 1,670, 720 by the phosphine-catalyzed dimerization of HDI, this gradual cleavage to reform HDI monomer can begin in the drying cabinet at temperatures of above 60° C.

To a lesser extent, in particular at temperatures above 150° C., this thermal stability problem also applies to allophanates which dissociate into more thermally stable urethane and isocyanate groups.

Low viscosity aliphatic polyisocyanates having optimal functionality can also be produced by alternative reactions, for example, by reacting silylized alcohols with isocyanatoalkanoic acid chlorides (Ch. Zwiener, L. Schmalstieg, M. Sonntag, K. Nachtkamp and J. Pedain, Farbe und Lack 1991, 1052–1057 and bibliography).

The disadvantage here is that isocyanatoalkanoic acid chlorides are not available industrially and they can involve handling problems. The process is very costly which outweighs the anticipated product advantages, primarily the low viscosity of the polyisocyanates.

Another disadvantage of isocyanurate polyisocyanates is their compatibility with certain polyols that are not sufficiently polar (DE-A 3,810,908). This can result in restriction on use, for example in the lacquers and coatings sector. According to the teachings of DE-A 3,810,908, this disadvantage may be overcome by terminating the trimerization while conversion is still low, thus obtaining isocyanurate polyisocyanates having at least 60 wt. % 1,3,5-tris(6-isocyanatohexyl) isocyanurate. However, this method is not advantageous for economic reasons as previously discussed.

An object of the present invention is to provide polyisocyanates, which are qualitatively at least equivalent to the isocyanurate group-containing polyisocyanate products, and either do not suffer or suffer to a lesser extent from the disadvantages of the prior art products.

This object may be achieved with isocyanate trimers according to the present invention.

SUMMARY OF THE INVENTION

The present invention relates to a polyisocyanate mixture containing isocyanate trimers provided that i) 30 to 100 mole percent of the trimers are iminooxadiazine diones B

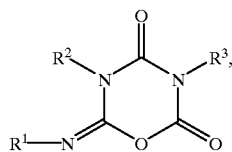

ii) 0 to 70 mole percent of the trimers are isocyanurates A,

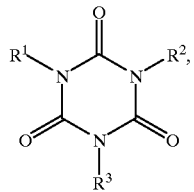

iii) less than 10 mole percent of the polyisocyanate mixture is of the uretone imine structural type G

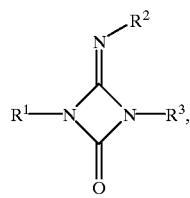

and iv) the ratio of the sum of the mole percents of trimers A and B to the mole percent of uretdiones F is greater than 4:1

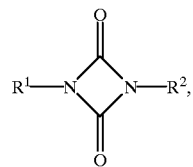

wherein $R^1$, $R^2$ and $R^3$ are the same or different and represent the groups obtained by removing an isocyanate group from an aliphatic, cycloaliphatic, aromatic and/or araliphatic isocyanate having an NCO content of less than 70% and/or their oligomers.

The present invention also relates to a process for the preparation of these isocyanate trimers by trimerizing at least a portion of the isocyanate groups of an aliphatic, cycloaliphatic, aromatic and/or araliphatic isocyanate having an NCO content of less than 75% in the presence of hydrogen (poly)fluoride catalysts corresponding to the formula $$M[nF^- (HF)_m]$$

wherein

M is an n-valent cation or an n-valent radical and
$m/n>0$, terminating the reaction at the required degree of trimerization and optionally removing unreacted isocyanate.

The present invention further relates to mixtures of these isocyanate trimers with polyisocyanates containing urethane, allophanate, urea, biuret, uretdione and/or oxadiazine trione groups.

Finally, the present invention relates to compositions containing these isocyanate trimers, in which the isocyanate groups may optionally be blocked with blocking agents, and compounds containing two or more isocyanate-reactive groups.

DETAILED DESCRIPTION OF THE INVENTION

In accordance with the present invention the term isocyanates refers to both monoisocyanates, polyisocyanates and mixtures of either or both of these types of isocyanates; the term trimers refers to pure trimers, e.g., trimer B as well as mixtures of different types of trimers, e.g, mixtures of A and B; and the term (cyclo)aliphatic isocyanate refers to isocyanates having aliphatically and/or cycloaliphatically bound isocyanate group(s).

The present invention is based on the extremely surprising observation that isocyanates can be converted into six-membered, heterocyclic systems not only by exclusively opening the C=N double bond, but also by opening the C=O double bond. This observation is highly surprising because in contrast to numerous publications relating to isocyanate secondary products which arise from opening the C=N double bond to form, e.g., isocyanurates and uretdiones, references to isomeric iminooxadiazine diones B are very rare.

Organically substituted diiminodioxazineones C and triiminotrioxanes D are entirely unknown, with the exception of cyanuric acid which is sometimes represented in the formula notation of D, $R^1$–$R^3$=H.

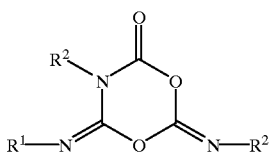

C

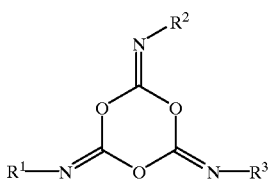

D

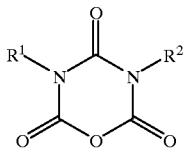

E

Only two representatives of class B have previously been isolated in pure form, the trimethyl derivative (3,5-dimethyl-2-methylimino-4,6-diketo-1,3,5-oxadiazine), B, $R^1$–$R^3$=Me (Chem. Ber. 1927, 60, 295) and 5-methyl-2-methylimino-3-phenyl-4,6-diketo-1,3,5-oxadiazine (Chem. Ber. 1987, 120, 339). In addition, the formation of B is known as a rare side reaction in the catalyzed oligomerization of aliphatic diisocyanates.

Thus, in the phosphine-catalyzed uretdione formation ("dimerization") of aliphatic diisocyanates at elevated temperatures with long reaction times and low catalyst concentration, in addition to a growing quantity of isocyanurates, there are also formed other by-products such as alkylimino-dialkyloxadiazine diones, carbodiimides and uretone imines (DE-A 1,670,720). A molar ratio of trimer (sum of A and B) to uretdione of less than 5:1 with phosphine catalysis can not be exceeded in the direction of higher trimer proportions if the occurrence of uretone imines G is to be avoided. On the other hand the molar proportion of iminooxadiazine dione B in the product and, in particular, the ratio of isocyanurate A to iminooxadiazine dione B remains virtually constant independently of the reaction conditions (see Example 1).

Uretone imines G are only usable to a certain extent for polyurethane preparation, because they dissociate ("cleave") to form diisocyanate monomer and carbodiimides at even lower temperatures than uretdiones. Uretone imines are present in dynamic equilibrium with carbodiimides at room temperature. If a diisocyanate monomer supplies the NCO group necessary to form G from a carbodiimide, the corresponding uretone imine causes a problem regarding the reformation of monomer, which means that safe use of resulting products is not possible for reasons of health and safety.

For this reason the literature always refers to carrying out the phosphine-catalyzed oligomerization of monomeric diisocyanates at the lowest possible temperature (cf. H. J. Laas et al., J. Prakt. Chem. 1994, 336, 196).

DE-A 3,902,078 describes a process for trimerizing (cyclo)aliphatic diisocyanates in the presence of carbon dioxide. In addition to oxadiazine triones E and isocyanates A, iminooxadiazine diones B are also formed, albeit to a lesser extent as is pointed out at p. 4, lines 51–52 of the cited patent specification. As may be seen from the examples of DE-A 3,902,078, the proportion of the latter, calculated on the proportion of trimer (sum of A and B, $R^1$–$R^3$=$(CH_2)_6$ $R^4$, wherein $R^4$ represents NCO and/or heterocycles of the structure A and/or B, which as opposed to $R^1$, $R^2$ and/or $R^3$ form direct links to the hexamethylene chain), does not exceed 25%. The same catalyst system and its use for the preparation of isocyanurate group-containing polyisocyanates is described in EP-A 0,355,479.

When trimerizing HDI with this catalyst system, even if the preparation conditions (co-catalysts, temperature, cation, etc.) are varied, the proportion of B in the trimer mixture (sum of A and B) is never greater than 25%; it is generally less than 20% (see Example 2).

It is disclosed in EP-A 0,355,479 that as a result of using the described catalyst systems for HDI trimerization at a resin yield of 20 or 60%, respectively, the dynamic viscosity, measured at 23° C. (hereinbelow $\eta^{23}$), is not below 1700 or 35,000 mPa•s, respectively. The isocyanurate polyisocyanates obtainable, for example, according to the teachings of DE-A 3,806,276 by catalysis with quaternary ammonium hydroxides exhibit $\eta^{23}$ values of approximately 1500 or 10,000 mPa•s at corresponding HDI trimer yields (cf. DE-A 3,806,276, Examples 6–12). Consequently the HDI trimers obtained by fluoride catalysis according to the teaching of EP-A 0,355,479 represent no improvement in terms of viscosity.

It is therefore surprising that when the proportion of B in a trimer mixture is increased significantly or when B alone is present, a drastic reduction in the viscosity of these products is obtainable.

In general, efforts to derive conclusions as to the viscosity of a certain compound or compound class from conclusions reached by analogy with other compounds or types of compounds is virtually impossible. Thus, for example, 1,3,5-tris(6-isocyanatohexyl) isocyanate A, $R^1$–$R^3$=$(CH_2)_6$—NCO, exhibits a considerably lower dynamic viscosity of approx. 700 mPa•s at 23° C., than 3,5-bis-(6-isocyanatohexyl)-1-oxadiazine trione E, $R^1$–$R^2$=$(CH_2)_6$—NCO, which is structurally related but only has an NCO functionality of 2 and has a $\eta^{23}$ value of approx. 1200 mPas (see Example 3).

A catalyst system suitable for preparing the trimers and trimer mixtures according to the invention is represented, for example, by hydrogen (poly) fluorides of the general composition $M[nF^-(HF)_m]$, wherein m/n>0 and M represents an n-charged cation (mixture) or one or more radicals which in total are n-valent. Some of these compounds are obtainable commercially or can be produced in simple manner and in any stoichiometry by blending corresponding fluorides with the desired quantity of HF.

Numerous references describe acids and acid derivatives as additives for terminating trimerization reactions (J. Prakt. Chem. 1994, 336, 185 et seq.). Therefore, it is extremely surprising that the catalytic activity of the catalysts is not destroyed, but on the contrary is increased decisively in its selectivity, by the addition of mineral acid HF, for example, to quaternary ammonium fluorides.

Hydrogen fluoride can, for example, be added as a solution in protic or aprotic organic solvents. HF amine complexes, for example with pyridine or melamine, are also available commercially. Unlike free hydrogen fluoride, which is unpleasant in physiological terms, hydrogen fluorides are not problematic. The presence of free hydrogen fluoride in the process products is also excluded by the known addition of HF to isocyanates, with formation of carbamoyl fluorides (J. Chem. Soc., 1945, 864–865).

The "HF constituent" of the catalyst systems described may vary within broad limits. That is to say it is unimportant whether it is constituted by defined monohydrogen difluorides, dihydrogen trifluorides, and the like, which are known, for example in the form of their potassium salts with the corresponding stoichiometry (Hollemann-Wiberg, Lehrbuch der Anorganischen Chemie [Inorganic Chemistry Textbook], 91st–100th editions, W. de Gruyter Verlag, Berlin, New York, 1985, p. 408, footnote 50) or by any mixtures of the latter compounds with excess fluoride on the one hand or HF on the other.

It is unimportant as regards the preparation of the trimers or trimer mixtures according to the invention whether the catalyst is soluble in the mono and/or polyisocyanate to be trimerized (homogeneous catalysis) or not (heterogeneous catalysis). Further substances or substance mixtures can also be added in the catalysis, for example amines, alcohols, phenols, solvents for the catalyst and/or the isocyanate, antioxidants, and matrices for adsorptive or covalent bonding of the catalyst. The hydrogen fluoride necessary for forming the hydrogen (poly)fluorides can also be added separately, optionally in dissolved form, to the isocyanate (mixture) to be trimerized, either before or during the trimerization. Furthermore, any substances which deliver hydrogen fluoride under the catalytic conditions, can be used to prepare the product (mixtures) according to the invention. Thus, for example, any carbamoyl fluorides are suitable as an "HF source" for the preparation of the trimers and trimer mixtures according to the invention.

The catalysis can take place within a temperature range of –80° C. to 550° C. in the condensed phase or in the gas phase, for example by quantitative conversion of the participating isocyanate groups of the starting (poly)isocyanate (mixture), or can be interrupted at any degree of conversion. In the latter case, all prior art methods described may be used to terminate the reaction. Examples include (hypo) stoichiometric quantities of acids or acid derivatives (for example benzoyl chloride, acid esters of phosphoric acid and phosphoric acid, and acids other than HF), adsorptive bonding of the catalyst followed by separation by filtration, thermal deactivation, etc. Catalyst concentrations of between a few ppm and 5%, based on the starting isocyanate, are sufficient for the preparation of the trimers (trimer mixtures) according to the invention.

According to a particular, optionally continuous, embodiment of the process, the trimers (trimer mixtures) according to the invention can be prepared in a tubular reactor. In this case there is additional advantages because the exothermic nature of the trimerization according to the invention is lower than that of conventional isocyanurate formation. The trimerization according to the invention may optionally be carried out with simultaneous urethanization and/or allophanization.

The trimers according to the invention can also be formed during the preparation (cross-linking reaction) of, optionally foamed, polyurethane plastics materials.

The trimers according to the invention may be prepared from any of the known aliphatic, cycloaliphatic, araliphatic and aromatic mono and polyisocyanates having an NCO content of less than 70%. The organic radicals present in these isocyanates may contain further substituents, such as carbonyl or carboxyl groups and heteroatoms (e.g., halogen, O, S, N, P, Si, Sn and B). Examples of suitable isocyanates include ethyl isocyanate and all regioisomers and stereoisomers of the following mono and polyisocyanates: propyl isocyanates, butyl isocyanates, hexyl isocyanates, octyl isocyanates, alkoxyalkyl isocyanates such as methoxypropyl isocyanate, cyclohexyl isocyanate, (methyl) cyclohexane diisocyanates, ethyl cyclohexane diisocyanates, propylcyclohexane diisocyanates, methyl diethyl cyclohexane diisocyanates, phenyl isocyanate, phenylene diisocyanates, tolyl isocyanates, tolylene diisocyanates, bis (isocyanatophenyl) methane, polyphenyl polymethylene polyisocyanates prepared, for example, by anilineformaldehyde condensation followed by phosgenation (MDI), propane diisocyanates, butane diisocyanates, pentane diisocyanates, hexane diisocyanates (HDI), heptane diisocyanates, octane diisocyanates, nonane diisocyanates and triisocyanates, decane diisocyanates and triisocyanates, undecane diisocyanates and triisocyanates, dodecane diisocyanates and triisocyanates, isophorone diisocyanate (IPDI), bis(isocyanatocyclohexyl) methane ($H_{12}$MDI), and isocyanatomethyl cyclohexanes (for example 4(3)-isocyanatomethylcyclohexyl isocyanate, "IMCI"). The process by which these (poly)isocyanates are prepared, i.e., with or without the use of phosgene, is not important.

It may be advantageous to utilize mixtures of certain isocyanates in the trimerization reaction according to the invention, for example, to match in optimal manner the property profile of the respective product or product mixture. Thus, mixtures of isocyanate polyisocyanates based on optionally branched-chain linear aliphatic diisocyanates (for example HDI) and cycloaliphatic diisocyanates (for example IPDI, $H_{12}$MDI) are utilized in many applications. These mixtures are generally prepared by blending separately prepared isocyanurate polyisocyanates.

It may be advantageous to prepare them by true mixed trimerization (EP-A 0,047,452). However, because prior art isocyanate polyisocyanates based on cycloaliphatic diisocyanates are solids at resin yields of less than 20% and sometimes exhibit such a high melt viscosity that it is very difficult to separate monomers by distillation, it is necessary to use solvents and occasionally also flow improvers during distillation to process them. Solution concentrations of around 70% are normal for cycloaliphatic diisocyanate-based isocyanurate polyisocyanates to obtain $\eta^{23}$ values of 1000–10 000 mPa•s.

When mixtures of linear aliphatic diisocyanates (for example HDI) and cycloaliphatic diisocyanates (for example IPDI) are trimerized with iminooxadiazine dione formation, products which are free-flowing even at room temperature are obtained ($\eta^{23} \leq 100\ 000$ mPa•s). These products additionally exhibit in solution a drastically more rapid decrease in viscosity with increasing solvent contents than for known isocyanurate products of a corresponding composition, i.e., functionality, diisocyanate starting material and average molecular weight. (see Example 4).

The viscosity of some of the trimers according to the invention based on optionally branched-chain, pure aliphatic diisocyanates, for example HDI, is also considerably lower than that of corresponding known products (see EP-A 0,047,452 and Example 5, infra).

The trimers according to the invention may be obtained in admixture with other isocyanate secondary products containing urethane ("prepolymer"), allophanate, urea, biuret, uretdione ("dimer") and/or oxadiazine trione structures, which can be separated by conventional prior art processes, such as thin film distillation, extraction, crystallization or molecular distillation. The resulting products are colorless or slightly colored liquids or solids having a melting range of approximately 30–180° C., depending on the isocyanates utilized.

A further advantage of the iminooxadiazine diones according to the invention resides in the reactivity of the heterocyclic ring system. The work by Slotta and Tschesche in their publication and Chem. Ber., 1927 60, 295, using the example of the trimethyl derivative B, $R^1$–$R^3$=Me, has made a significant contribution in this context.

Thus, when the compound reacts with water the, ring is opened, and decarboxylation forms 1,3,5-trimethyl biuret, a compound which is readily biodegradable. Alcoholysis or aminolysis, which have not previously been described, yield urea-3-(carboxylic acid amide)-1-(carboxylic acid ester) or triurets, respectively.

These classes of compound are accessible only with difficulty by alternative routes (cf. A. Botta in "Houben/Weyl, Methoden der Organischen Chemie" supplements and further volumes to 4th Edition, Vol. E4, Carbonic Acid Derivatives, G. Thieme Verlag, Stuttgart, N.Y., 1983 ed. H. Hagemann, pp. 1325–1334), and they may be of value in both the active ingredients and the polyurethanes sector.

In the polyurethanes sector, it is possible, for example, to recover valuable NCO groups, which were initially consumed in the trimerization reaction, for subsequent cross-linking to form high molecular weight plastics or coatings. If these reactions are, for example, carried out with iminooxadiazine diones B which still contain NCO groups in the substituents $R^1$–$R^3$, and (poly)hydroxy-functional products such as polyethers or polyesters, the ring-opening reaction and optionally the subsequent dissociation reaction of the tricarbonyl compounds can be used in a targeted manner to obtain isocyanurate-free plastics materials, coating agents or additives which meet stringent demands as to biodegradability. Such products are of particular interest for imparting wet strength to paper, for example. In addition, the NCO functionality of ideal diisocyanate trimers of the general formula A or B ($R^1$–$R^3$=R'—NCO wherein R' is an NCO-group-free organic radical) increases from 3 in the case of A to up to 5 in the case of B.

A further advantage of the iminooxadiazine diones according to the invention resides in the isomerization to A. Thus, at room temperature and sometimes even far below room temperature, it is possible in simple manner to undertake the rearrangement of the iminooxadiazine dione structure into the isomeric isocyanurate structure. This may be achieved while simultaneously reacting the NCO groups with Zerewitinoff-active-hydrogen-containing compounds, optionally in the presence of catalysts, to obtain plastics materials and coatings which have the same high property level of prior art isocyanurate polyisocyanates, but which provide the aforementioned viscosity advantages both before and during the application.

The compounds and mixtures according to the invention consequently represent versatile starting materials for the preparation of active ingredients and optionally foamed plastics materials and for the preparation of lacquers, coating compositions, adhesives and additives. They are in particular suitable, optionally in NCO-blocked form, for the preparation of one- and two-component polyurethane coating compositions due to their solvent viscosity and melt viscosity which are lower than those of (predominantly) isocyanurate polyisocyanate-based products and, in addition, provide a property profile which is in other respects equal or better.

In this latter field of application they may be utilized, either pure or in conjunction with other prior art isocyanate derivatives such as uretdione, biuret, allophanate, isocyanurate, urethane and carbodiimide polyisocyanates in which the free NCO groups have optionally been deactivated with blocking agents.

A further advantage of the trimers according to the invention resides in the fact that they exhibit no tendency to dissociate into the monomeric (poly)isocyanates on which they are based, even under prolonged thermal load. Thus, even compounds having boiling points as high as that of tris(6-isocyanatohexyl) iminooxadiazine dione B, $R^1$–$R^3$= $(CH_2)_6NCO$, can be separated by both distillation and also extraction from the HDI trimer mixtures according to the invention, without undergoing decomposition or rearrangement to the isomeric isocyanurate A, $R^1$–$R^3$=$(CH_2)_6$. This results in products having viscosities substantially below the viscosity of 700 mPa•s given in the literature for 1,3,5-tris (6-isocyanato-hexyl) isocyanurate A, $R^1$–$R^3$=$(CH_2)_6NCO$ (see Example 6). Therefore, tris(6-isocyanatohexyl) iminooxadiazine dione B, $R^1$–$R^3$=$(CH_2)_6NCO$, is the lowest viscosity NCO-trifunctional oligomer of hexamethylene diisocyanate.

The polyisocyanate trimers according to the invention are also suitable for applications having a dual cross-linking mechanism. For example, the free reactive groups, generally isocyanate groups, are reacted with a polyol component or polyamine component in a first reaction step, and in an independent second step a further cross-linking is carried out with breakdown of the iminooxadiazine dione structure. The means, as previously discussed, that up to two isocyanate-reactive groups can be reacted per equivalent of iminooxadiazine dione unit.

The resulting plastics and coatings largely correspond structurally to those which are obtained from biuret or allophanate group-containing raw materials, on the one hand, and isocyanurate group-containing raw materials, on the other hand. They are exceptionally high grade products having the property profile which is typical of the proven prior art systems, without the disadvantages previously discussed.

The polyisocyanate trimers according to the invention are suitable for use as binders in coating compositions. They are preferably utilized, optionally blended with other polyisocyanates and optionally in blocked form, as a cross-linking component in, optionally aqueous, one- and two-component coating compositions. When used as a cross-linking component in two-component coating compositions, the polyisocyanates according to the invention are generally combined with known OH components and NH components, such as hydroxy-functional polyesters, polyacrylates, polycarbonates, polyethers and polyurethanes, and polyfunctional amines. They may also be used in one-component coating compositions to prepare moisture-curing plastics and coatings.

The coating compositions may also contain additives such as wetting agents, flow promoters, anti-skinning agents, antifoaming agents, flatting agents, viscosity regulators, pigments, dyes, UV absorbents, catalysts and thermal and oxidative stabilizers. They may also contain solvents or solvent mixtures such as toluene, xylene, cyclohexane, chlorobenzene, butyl acetate, ethyl acetate, ethyl glycol acetate, methoxypropyl acetate, acetone, white spirit and higher-substituted aromatics (such as Solvent Naphtha, Solvesso, Schellsol, Isopar, Nappar and Diasol solvents).

The polyisocyanates based on the trimers according to the invention may be used to prepare coatings or may be used as an additive for finishing a variety of materials such as wood, plastics, metals, leather, paper, concrete, masonry, ceramics and textiles.

EXAMPLES

In the following examples all parts and percentages are by weight unless otherwise indicated. The dynamic viscosities were determined at 23° C. using the VT 550 plate-cone viscometer, measuring arrangement PK 100, ex Haake. Measurements were carried out at different gravitational velocities to ensure that the flow characteristics of the described polyisocyanate mixtures according to the invention, and also those of the comparative products, correspond to those of ideal newtonian fluids. Indicating the gravitational velocity is therefore superfluous.

Example 1

Comparison Example Using Phosphine Catalysis

Three 200 g (1.19 mol) portions (1a, 1b and 1c) of freshly distilled HDI were first stirred at 60° C. for 1 hour under vacuum (0.1 mbar) to remove dissolved gases, followed by aeration with dry nitrogen, and then at temperatures of a) 60° C. (1a)

b) 120° C. (1b) and c) 180° C. (1c), respectively, 3 g (14.8 mmol) of tri-n-butyl phosphine (ex Acros, late Janssen) were added in each case and the mixtures were reacted in a nitrogen atmosphere until the refractive index of the crude solution reached the value set forth in Table 1. The reaction was then terminated by the addition in each case of 4 g (26 mmol) of p-toluene sulphonic acid methyl ester, while stirring continued at 80° C. for approximately one hour until there was no further change in the refractive index of the mixture (cf. Table 1).

Unreacted monomer was then removed from the crude products by thin film distillation at 120° C./0.1 mbar in a short-path evaporator. The product composition was then determined by NMR spectroscopy and the residual monomer content by gas chromatography. The latter was determined again after storage for 3 weeks at room temperature (20–25° C.), and after storage for a further 2 weeks at 50° C. in a drying cabinet. All of the analytical results are set forth in Table 1.

Example 2

Comparison Example Using Fluoride Catalysis

Four 200 g (1.19 mol) portions (2a, 2b, 2c and 2d) of freshly distilled HDI were stirred at 60° C. for 1 hour under vacuum (0.1 mbar) to remove dissolved gases, aerated with dry nitrogen, and then treated as follows:

2a) At 80° C. approximately 900 ppm, based on the weight of the catalyst and HDI, of an approx. 8% catalyst solution of N-methyl-N,N,N-trialkyl ammonium chloride containing $C_{8-10}$ alkyl groups (Aliquat 336, available from Fluka, GmbH) in 2-ethyl-1,3-hexanediol, prepared as described in Example 1 of DE-A 3,902,078 (U.S. Pat. No. 5,013,838, herein incorporated by reference) were added. The temperature rose to 105° C. and the mixture was stirred until an NCO content of 41.2% was reached. The reaction was terminated by the addition of 0.9 g phosphoric acid di-n-butyl ester with stirring for a further hour at 60° C. Unreacted monomer was then removed by thin film distillation at 120° C./0.1 mbar in a short-path evaporator. The product composition and residual monomer content were determined as in Example 1.

2b) The procedure was the same as in 2a), except that 110 ppm of a 5% catalyst solution of tetramethylammonium fluoride tetrahydrate (ex Aldrich) in n-butanol were used as the catalyst, the trimerization reaction was carried out at a temperature of 60 to 70° C., and the reaction was terminated at an NCO content of 39.1% by the addition of 0.132 g of phosphoric acid di-n-butyl ester.

2c) The procedure was the same as in 2a), except that 190 ppm of an 8.3% solution of tetraethylammonium fluoride hydrate (ex Aldrich) in n-butanol were used as the catalyst, the trimerization reaction was carried out at a temperature of 70 to 150° C., and the reaction was terminated at an NCO content of 39.9% by the addition of 0.312 g of phosphoric acid di-n-butyl ester;

2d) The procedure was the same as in 2a), except that 160 ppm of a 5% solution of benzyl trimethylammonium fluoride hydrate (ex Aldrich) in 2-ethyl-1,3-hexanediol (ex Janssen) were used as the catalyst and the trimerization reaction was terminated at an NCO content of 35.1% by the addition of 0.03 g of phosphoric acid di-n-butyl ester.

| Experiment | $N^{20}_D$ (stop) | Resin Yield [%] | Viscosity [mPa.s] | Residual monomer content [%] | Uretone imines G [%] | Uretdiones [mole %] | Isocyanurates A [mole %] | Iminooxadiazine dioties B [mole %] | Ratio of trimers (A + B): uretdiones | Ratio A:B |
|---|---|---|---|---|---|---|---|---|---|---|
| 1a | 1.4732 | 46.3 | 240 | 0.1/0.1/0.2[1] | n.d[2] | 69 | 22 | 9 | 0.45 | 2.4 |
| 1b | 1.4731 | 40.0 | 1250 | 0.3/0.3/0.4[1] | 3 | 28 | 47 | 22 | 2.5 | 2.1 |
| 1c | 1.4768 | 39.4 | 5200[3] | 2.7/3.8/5.4[1] | 54 | 4 | 30 | 12 | 10.5 | 2.5 |

Table 1

Results of tributyl phosphine-catalyzed HDI oligomerization at different temperatures 1) Residual monomer content after distillation/after storage for 3 weeks at room temperature/after further storage for 2 weeks at 50° C.

2) n.d.=not detectable 3) heterogeneous, turbid product

| Experiment | Resin yield [%] | Resin NCO content [%] | Viscosity [mPa·s] | Residual monomer content [%] | Isocyanurates A [mole %] | Iminooxadiazine diones B [mole %] | Urethanes [mole %] | Allophanates [mole %] | Uretdiones [mole %] | Ratio A:B |
|---|---|---|---|---|---|---|---|---|---|---|
| 2a | 32.1 | 22.5 | 2000 | 0.17 | 68 | 14 | n.d. | 13 | 3 | 83:17 |
| 2b | 36.5 | 22.8 | 2300 | 0.08 | 74 | 18 | n.d. | 5 | 3 | 80:20 |
| 2c | 39.4 | 22.4 | 2080 | 0.1 | 69 | 21 | 2 | 5 | 3 | 77:23 |
| 2d | 47.3 | 21.1 | 5800 | 0.13 | 69 | 15 | 2 | 10 | 4 | 82:18 |

Table 2
Results of fluoride-catalyzed HDI trimerization

The products frequently exhibited turbidity in either the crude product or the monomer-free resin, such that filtration was necessary before or after thin film distillation. After protracted storage of the resins, even when filtration had taken place before or after thin film distillation, turbidity frequently reoccurred. As Table 2 indicates, the molar proportion of B in the trimer mixture (sum of A and B) was always far below 30%.

Example 3 (Comparison Example)

1500 g of a) an HDI-isocyanurate polyisocyanate having an NCO content of 23.5% and a viscosity of 1380 mpa•s, prepared according DE-A 3,806,276, and b) an HDI-oxadiazine trione polyisocyanate having an NCO content of 22.5% and a viscosity of 2560 mpa•s, prepared according to DE-A 1,670,666, were each subjected to thin film distillation in a short-path evaporator at a pressure of 0.05 mbar and a temperature of 220° C. 364 g were collected in a) and 1092 g were collected in b). HDI was then removed from each of the collected products by film distillation at 120° C. The resulting products exhibited the following viscosities:

Product a), which is the ideal isocyanurate trimer of hexamethylene diisocyanate (1,3,5-tris(6-isocyanatohexyl) isocyanurate A, $R^1$–$R^3$=$(CH_2)_6$—NCO), had a viscosity of 700±10 mPa•s at 23° C.

Product b), which is 3,5-bis(6-isocyanatohexyl)-1-oxadiazine trione E, $R^1$ and $R^2$=$(CH_2)_6$—NCO, had a viscosity of 1200±20 mpa•s at 23° C. Determination by combined analytical methods (IR, NMR, GPC, MS) showed a purity of at least 98%.

The measurements taken on A were in complete agreement with data disclosed in the literature (cf. WO-A 93/07,183, the viscosities quoted in the Examples therein were measured at 25° C. on less pure "ideal isocyanurate" fractions). No data was available in the literature for comparison with E.

Example 4 (according to the invention)

In a 250 ml four-necked flask having an internal thermometer, stirrer, reflux condenser, gas inlet tube and dispensing device for the catalyst solution, gases dissolved in the diisocyanate mixture were first removed from a mixture of 84 g (0.5 mol) of HDI and 111 g (0.5 mol) of isophorone diisocyanate (IPDI) at room temperature and at a pressure of approx. 0.1 mbar over the course of one hour. The mixture was then heated to an internal temperature of 60° C. while nitrogen was passed through. At this temperature a total of 1.614 g (920 ppm) of a solution of 0.5 g tetraethylammonium fluoride hydrate (ex Aldrich) and 0.2 g of hydrogen fluoride in 5.6 g of 2-ethyl-1,3-hexanediol were then added dropwise over the course of approx. 20 minutes, such that the internal temperature did not exceed 70° C. The mixture was trimerized at 60–70° C. until the NCO content of the mixture was about 34.2%. and then the reaction was terminated by the addition of 0.181 g of di-n-butyl phosphate while the mixture was stirred for an additional hour at 60° C. Unreacted monomeric diisocyanates were then separated by film distillation in a short-path evaporator at 0.1 mbar and a temperature of 170° C. The composition of the diisocyanate mixture distilled off was 65 mol. % IPDI and 35 mol. % HDI.

A clear, almost colorless resin was obtained (62.4 g corresponding to a 32% yield) having a viscosity of 26,500 mPa•s, an NCO content of 18.8% and residual monomer contents of 0.13% HDI and 0.27% IPDI. The molar ratio of isocyanurates A to iminooxadiazine diones B was 1:1, wherein $R^1$–$R^3$ represent difunctional alkyl radicals obtained by removing the isocyanate groups form HDI and/or IPDI, wherein the alkyl radicals contain NCO, isocyanurate, iminooxadiazine dione, uretdione, urethane and/or allophanate groups in the terminal position.

Example 5 (according to the invention)

2000 g of HDI were first pretreated as described in Example 4, then a total of 17.23 g (520 ppm, based on the weight of the catalyst and HDI) of a 6% catalyst solution in 2-ethyl-1,3-hexanediol of the catalyst described in Example 2a), present in admixture with HF at a molar ratio of 1:5, was added. The catalyst was prepared as described in DE-A 3,902,078, Example 1, (U.S. Pat. No. 5,013,838) except that the corresponding quantity of HF was added subsequently as a separately prepared solution in 2-ethyl-1,3-hexanediol). The catalyst was added dropwise over a period of 90 minutes at an initial internal temperature of 50° C., such that the internal temperature did not exceed 65° C. When the NCO content of the mixture was 40%, 0.22 g of dibutyl phosphate were added, the mixture was stirred for a further hour at 50° C. and then it was worked up as described in Example 4. 720 g (corresponding to a 36% resin yield) of a colorless, clear trimer mixture were obtained having the following properties:

NCO content: 22.8%
viscosity: 1490 mpa•s
residual monomer content: 0.17% HDI
molar ratio A:B: 1:1

Example 6 (according to the invention)

570 g of the product obtained according to Example 5 were distilled and purified to remove HDI under the conditions set forth in Example 3. 125 g of a trimer mixture (sum of A and B, $R^1$–$R^3$=$(CH_2)_6$—NCO) of over 98% purity were obtained having a ratio of A to B which was unchanged from the starting oligomer mixture. The viscosity of this mixture was 380 mPa·s, which is substantially less than the viscosity of 700 mPa·s reported for the pure trimer A in Example 3.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate mixture containing isocyanate trimers wherein i) 30 to 100 mole percent of the trimers are iminooxadiazine diones B

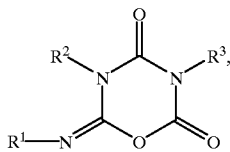

ii) 0 to 70 mole percent of the trimers are isocyanurates A,

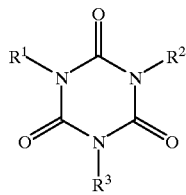

iii) less than 10 mole percent of the polyisocyanate mixture are uretone imines G

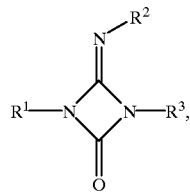

and iv) the ratio of the sum of the mole percents of trimers A and B to the mole percent of uretdiones F is greater than 4:1

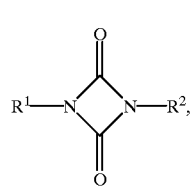

wherein $R^1$, $R^2$ and $R^3$ are the same or different and represent the groups obtained by removing an isocyanate group from an aliphatic, cycloaliphatic, aromatic and/or araliphatic isocyanate having an NCO content of less than 70%.

2. The polyisocyanate mixture of claim 1 wherein $R^1$, $R^2$ and $R^3$ represent the groups obtained by removing an isocyanate group from a (cyclo)aliphatic diisocyanate.

3. The polyisocyanate mixture of claim 1 wherein $R^1$, $R^2$ and $R^3$ represent the groups obtained by removing an isocyanate group from 1,6-hexamethylene diisocyanate and/or isophorone diisocyanate.

4. A process for the preparation of the polyisocyanate mixture of claim 1 which comprises trimerizing at least a portion of the isocyanate groups of an aliphatic, cycloaliphatic, aromatic and/or araliphatic isocyanate having an NCO content of less than 75% in the presence of a hydrogen (poly)fluoride catalyst corresponding to the formula $$M[nF^- (HF)_m]$$

wherein

M is an n-valent cation or an n-valent radical and
m/n is >0, terminating the reaction at the required degree of trimerization and optionally removing unreacted isocyanate.

5. A composition containing the polyisocyanate mixture of claim 1 in admixture with one or more polyisocyanates containing urethane, allophanate, urea, biuret, uretdione and/or oxadiazine trione groups.

6. A composition containing the polyisocyanate mixture of claim 1, in which the isocyanate groups may optionally be blocked with blocking agents, and a compound containing two or more isocyanate-reactive groups.

* * * * *